United States Patent [19]

Müller

[11] 4,017,454

[45] Apr. 12, 1977

[54] GLASS CERAMIC AS FILLER IN POLYMERIZABLE DENTAL FILLING COMPOSITIONS

[75] Inventor: Gerd Müller, Mainz-Weisenau, Germany

[73] Assignee: Jenaer Glaswerk Schott & Gen., Mainz, Germany

[22] Filed: Feb. 6, 1976

[21] Appl. No.: 655,963

Related U.S. Application Data

[62] Division of Ser. No. 505,146, Sept. 11, 1974, Pat. No. 3,973,972.

[30] Foreign Application Priority Data

Sept. 21, 1973 Germany .......................... 2347591

[52] U.S. Cl. .................. 260/42.52; 32/15; 260/42.43; 260/998.11
[51] Int. Cl.² .......................................... C08K 3/34
[58] Field of Search ....... 260/42.52, 998.11, 42.43; 32/15

[56] References Cited

UNITED STATES PATENTS

| | | | |
|---|---|---|---|
| 3,808,170 | 4/1974 | Rogers | 260/998.11 |
| 3,911,581 | 10/1975 | Dietz | 260/998.11 |

FOREIGN PATENTS OR APPLICATIONS 2,132,788 0000 Germany

*Primary Examiner*—James H. Derrington
*Attorney, Agent, or Firm*—Millen & White

[57] ABSTRACT

Transparent, colorless glass ceramic having a low coefficient of expansion, a high absorptivity for X-rays and which is useful in dental filling compositions, has the following ingredients, expressed as percent by weight of oxides: $SiO_2$ 40–55%, $Al_2O_3$ 15–25%, $Li_2O$ 3–5%, $P_2O_5$ 3–10%, MgO 0–3%, ZnO 0–5%, $ZrO_2$ 2–7%, $Ta_2O_5$ 0–7% and $La_2O_3$ 10–20%.

15 Claims, No Drawings

GLASS CERAMIC AS FILLER IN POLYMERIZABLE DENTAL FILLING COMPOSITIONS

This is a division of application Ser No. 505,146, filed Sept. 11, 1974, now U.S. Pat. No. 3,973,972, issued Aug. 10, 1976.

BACKGROUND OF THE INVENTION

This invention relates to radiopaque colorless glass ceramics, to compositions comprising such glasses and a polymerizable synthetic resin, and in particular to such compositions useful for dental fillings. To replace the conventional amalgam or gold dental fillings, compositions have been developed based on rapidly polymerizable synthetic resins, e.g., acrylate or methacrylate, and a pulverulent inorganic material, e.g., glass, embedded in the synthetic resin.

Heretofore, two groups of inorganic fillers have been added to the synthetic resins: (a) glasses distinguished by relatively high contents of BaO (cf. the article by Bowen and Cleek in "Journal of Dental Research," 1972, pp. 177–182); and (b) Li-Al silicates (DOS [German Unexamined Laid-Open Application] 1,570,971). The reason for the use of BaO-containing glasses is that barium exhibits a high absorption of short wavelength X-ray radiation, as utilized in dental diagnostics. As a result thereof, the composite synthetic resin-Ba-glass element has an absorption which clearly distinguishes same from the surrounding, natural tooth material or even from possible cavities.

The second group of fillers, namely the Li-Al silicates, do not possess this advantageous, high X-ray absorption, but, instead are distinguished by very low, frequently even negative, coefficients of thermal expansion. This property is very desirable insofar as low coefficients of thermal expansion of the filler material can compensate for the very high coefficients of expansion of the synthetic resins, so that the average coefficient of thermal expansion of the synthetic resin-Li-Al-silicate composite can easily be adapted to that of natural tooth substance. This is a very important advantage, since otherwise there is the danger that exposure to sudden temperature changes would result in mechanical stress within the tooth or mechanical stress which might even cause an unloosening of the filling from the tooth. (To avoid this problem, ground quartz glass, as well as Li-Al silicates, has also been utilized as the filling material.)

Whereas it would be desirable to provide a glass having both the desired high X-ray absorption and the described low coefficient of expansion, heretofore, no materials have been known which would sufficiently satisfy this combination of requirements. In glasses, a low thermal expansion can normally be attained only with very high contents of $SiO_2$ which, in turn, cannot be coupled with the requirement of a high X-ray absorption. The number of other solid substances of very low thermal expansion is relatively limited. Among these substances, insofar as they are sufficiently resistant to chemicals, there is not a single one with a high X-ray absorption.

SUMMARY OF THE INVENTION

An object of this invention therefore, is to provide a material exhibiting a sufficiently high X-ray absorption and a sufficiently low thermal expansion for dental filling purposes. Whereas the material may have other uses as well, for dental fillings, it should not contain soluble toxic components and it must be sufficiently resistant chemically. It must furthermore be substantially, if not completely, transparent and colorless, so that pigmentation can render the finished product close to that of natural teeth. Furthermore, it should be possible to employ the material in high volumetric proportions in the polymerizable synthetic resin, and of course, it is necessary that sufficient adhesion be established between the filling material and the synthetic resin. Also, the material must be relatively abrasion-resistant and hard.

Other objects relating to such a material are to provide a starting composition and a method for its manufacture.

Aside from providing the material itself, another object of this invention is to provide a polymerizable mixture of the material with a synthetic polymer.

A still further object is to provide articles made from said polymerizable mixture.

Upon further study of the specification and appended claims, further objects and advantages of this invention will become apparent to those skilled in the art.

To attain these objects, it has now been found that it is possible to employ glass ceramics as fillers for polymerizable dental filling compositions. These are glass-crystal mixed bodies built up of glass and one or more types of crystals precipitated from the glass by controlled crystallization. Such substances can be transparent if the indices of refraction of the various types of crystals and of the glass do not differ too much, e.g., by not more than about 0.05, preferably not greater than 0.01, or if the thus-precipitated crystals are sufficiently small, e.g. having a particle size less than about 1000A, preferably less than 500 A. The Li-Al silicates mentioned in the foregoing can be produced in the form of transparent glass ceramics, but not in the pure form. For, in order to produce fine-grained glass ceramics, additions of so-called nucleating agents are required for the formation of a multitude of crystallization nuclei so that the resultant fine crystals are uniformly distributed in the volume. In case of Li-Al silicate glasses, the addition of $TiO_2$, often in conjunction with $ZrO_2$, leads to glass ceramic having such a tiny crystal size that they are transparent. Unfortunately, the $TiO_2$ content causes a marked brown coloring which is undesirable for the use of such glass ceramics in dental filling compositions. When abandoning the simple basic system of $Li_2O-Al_2O_3-SiO_2$ and introducing a number of additional components into the starting glass materials, it is also possible to obtain an extremely effective nucleus formation by means of other oxides, among which are also those which do not impart a coloring. Such glass ceramics have been described in German Patent 2,132,788. Among these is also a group which can contain up to 12% by weight of oxides of the rare earths. The contents of this German patent are incorporated by reference herein.

It has now been found surprisingly that the rare earth oxide content of the glasses in the German patent can even be increased substantially above 12% by weight without losing the advantageous properties, particularly the transparency and the low thermal expansion, insofar as such method is restricted to the production of glass ceramic in a fine-granular form, either as small spheres according to one of the conventional spraying or centrifugal processes, or as a granulated material formed by the introduction of a thin stream of glass into cold water.

It is known that, by the rapid cooling which takes place in the aforementioned methods, clear glasses can also be obtained even in those cases wherein the production of larger molded articles is no longer possible, due to the tendency toward turbidity or crystallization displayed by the glass. However, it was surprising that the transparency of the crystallized glass ceramic is not lost upon a further increase of the content of those oxides which are foreign to the primary crystalline phases of the glass ceramic, and that, moreover, the thermal expansion does not rise unduly, since both of these phenomena are customarily encountered.

The rare earth atoms are distinguished, insofar as they do not belong to the extremely heavy elements with the highest atomic numbers, by a very high absorptive power for X-rays of the wavelength of about 0.2 – 0.3 A (this range being predominantly employed in dentistry). Consequently, even glass ceramics having proportions of at least 10% by weight, advantageously more than 12%, especially over 15% by weight, of such oxides, exhibit a very satisfactory absorbability. The upper limit for the rare earth content is about 20%, preferably 17%. Such glass ceramics are highly suitable for dental filling compositions, especially if lanthanum is utilized as the rare earth, for lanthanum forms colorless ions and exhibits and excellent absorption of X-rays having wavelengths of around 0.3 A. Moreover, $La_2O_3$ is inexpensive as compared to the heavier rare-earth oxides.

Accordingly, the glass ceramic of this invention have the following composition (in % by weight):

| | |
|---|---|
| $SiO_2$ | 40 – 55 |
| $Al_2O_3$ | 15 – 25 |
| $Li_2O$ | 3 – 5 |
| $P_2O_5$ | 3 – 10 |
| MgO | 0 – 3 |
| ZnO | 0 – 5 |
| $ZrO_2$ | 2 – 7 |
| $Ta_2O_5$ | 0 – 7 |
| $La_2O_3$ | 10 – 20 |

Preferably, the glass ceramics of this invention have the following compositions (in % by weight):

| | |
|---|---|
| $SiO_2$ | 40 – 50 |
| $Al_2O_3$ | 16 – 20 |
| $Li_2O$ | 3.3 – 4.7 |
| $P_2O_5$ | 4 – 7 |
| MgO | 0 – 2 |
| ZnO | 0 – 5 |
| $ZrO_2$ | 3 – 6 |
| $Ta_2O_5$ | 2 – 6 |
| $La_2O_3$ | 13 – 18 |
| MgO + ZnO | 1 – 7. |

The presence of MgO and ZnO substantially improves the transparency of the glasses of the invention.

$Ta_2O_5$ in combination with $ZrO_2$ acts as nucleating agent, which considerably reduces the grain size of the crystallites in the glass ceramic of the invention.

In addition to the aforementioned oxides, additional oxides can be contained in the composition, insofar as they are non-toxic and do not impair the other properties of the glass ceramic. The melting characteristics can be improved without noticeable disadvantages by the introduction of $Na_2O$ and/or $K_2O$ in amounts of up to 1% by weight. The total content of possible additional components should preferably not exceed 5% by weight, for otherwise it would be difficult to maintain the properties according to this invention. The glasses are produced in a conventional manner, as described in German Pat. No. 2,132,788.

The conversion of these glass ceramics from the glassy into the partially crystalline condition is straightforward; it is sufficient to heat the glass at a rate of about 6°/minute or less from a temperature of about 0° C to 600° C, to temperatures of at least 800° C. and at most about 900° C., and to leave the glass at this final temperature for annealing for about 1 to 5 hours. Annealing can be conducted at lower temperatures, but longer annealing times are required, for example about 10 hours at 750° C. The extremely high number of nuclei necessary to obtain a transparent glass ceramic is attained very rapidly with these glasses, i.e. during the heating step, and thus does not require any special measures.

After crystallization, the glass ceramics have thermal expansions (range 0° – 50°) of between —10 and +20 · $10^{-7}$ degrees$^{-1}$; they are colorless and transparent. As for the types of crystals, they contain mixed crystals with a high-quartz structure in a proportion estimated according to the intensities of X-ray diffraction diagrams, of about 30–40% by weight, and furthermore mixed crystals of the structural type of cubic $ZrO_2$, and a compound containing $La_2O_3$ which heretofore has not been known in detail. Overall, the percent by weight crystallinity of the glass is about 30 to 70, preferably 40 to 50.

The glass ceramics can be silanized in the usual manner, as has also been done in the fillers utilized heretofore, to provide good adhesion to the synthetic resin. The particle size of the glass ceramics for dental purposes is usually in the range of 5 to 100, preferably 5 to 60 microns.

The X-ray mass absorption coefficient (0.2 – 0.3 A) of the glass ceramics is about 3 to 7.

A wide variety of synthetic polymerizable resins can be employed in this invention, both those presently available as well as those available in the future. Consequently, it is not even possible to catalog a complete list of specific monomer-polymer systems useful in the context of this invention. Suffice it to note that all polymers can be reinforced with glass ceramic of this invention. For dental purposes in particular, attention is directed to the patent and technical literature for specific suggestion of synthetic resins, catalysts, monomers, oligomers, polymers, adducts, initiators, etc. which can be incorporated into a system used in making dental fillings or in the production of dental prosthetic devices.

With respect to the proportions by volume of the glass ceramic in the synthetic resin, a wide range can be employed, e.g., about 20 to 70% of the total composition being the ceramic glass. For example, with acrylics (including acrylic and methacrylic acid esters thereof and glycidyl adducts thereof), considerable amounts of powders or spherical particles of these glass ceramic are incorporated, normally more than 50% by volume. The exact upper limit of glass ceramic which can be incorporated into the composite body depends on the geometrical form and the particle size distribution of the particulate glass ceramic, but is sufficiently high in all cases that a satisfactory adaptation of the expansion of the composite article to that of natural tooth material is possible.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The following table describes examples of glass ceramics of this invention with their compositions and properties.

TABLE

Examples for Radiopaque, Colorless Glass Ceramics

| % by Weight | No.1 | No. 2 | No. 3 | No. 4 |
|---|---|---|---|---|
| $SiO_2$ | 45.2 | 48.3 | 49.0 | 52.0 |
| $Al_2O_3$ | 21.7 | 17.7 | 18.7 | 16.0 |
| $P_2O_5$ | 8.2 | 4.5 | 5.0 | 4.0 |
| $Li_2O$ | 4.7 | 4.0 | 4.0 | 4.0 |
| $K_2O$ | 0.6 | — | — | — |
| MgO | 1.0 | — | — | — |
| ZnO | 1.3 | 2.0 | 3.3 | 1.0 |
| $ZrO_2$ | 5.0 | 5.0 | 5.0 | 5.0 |
| $Ta_2O_5$ | — | 2.5 | 2.5 | 5.0 |
| $La_2O_3$ | 12.3 | 16.0 | 12.5 | 13.0 |
| Heat Treatment: | 3 h 900° | 3 h 720° +2 h 850° | 3 h 720° +2 h 850° | 5 h 800° C. |
| $\alpha$ 0°–50° ($10^{-7}$ degree$^{-1}$) | +3.0 | +6.5 | +4.0 | +5.5 |

To illustrate the production of the glass ceramics of the invention the following example is given:

For the production of the glass of example 3 appropriate amounts of the following raw materials - chemical grade - are thoroughly blended:

$SiO_2$, $Al(OH)_3$, $Al(PO_3)_3$, $Li_2CO_3$, ZnO, $ZrO_2$, $Ta_2O_5$, and $La_2O_3$.

This batch is melted in a quartz crucible for 3 hours at 1550° C, and is poured into cold water to obtain finely divided glass beads, which are then remelted for 2 hours at 1550° C, and are again poured into cold water. Thereafter, the glass beads are heated at a rate of 1° C/min. to 720° C, are maintained at 720° C for 3 hours, are further heated with 1° C/min. to 850° C, are again maintained for 2 hours, and are removed from the furnace.

The following recipe is a polymerizing dental filling composition according to the present invention:

Dental Filling Composition (Rapidly Polymerizing Two-Component System)

Component A

40% Glycidyl methacrylic acid adduct
4% Triphenylborane ammonia complex (cocatalyst)
4% Benzoyl peroxide (catalyst)

Component B

12% Metharcylic acid

Filler (Divided between components A and B):
40% glass ceramic No. 4 of the table.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a dental filling composition consisting essentially of organic compound polymerizable into a synthetic resin and particles of a glass ceramic, the improvement comprising employing as said glass ceramic particulate colorless, transparent glass ceramic having a particle size of 5–100 microns, having about 30–70% crystallinity by weight, a thermal expansion of less than $20 \cdot 10^{-7}$ degree$^{-1}$ (0° – 50° C.) and exhibiting absorption for X-rays, said glass ceramic consisting essentially of, in percent by weight based on oxides:

| $SiO_2$ | 40 – 55 |
|---|---|
| $Al_2O_3$ | 15 – 25 |
| $P_2O_5$ | 3 – 10 |
| $Li_2O$ | 3 – 5 |
| MgO | 0 – 3 |
| ZnO | 0 – 5 |
| $ZrO_2$ | 2 – 7 |
| $Ta_2O_5$ | 0 – 7 |
| $La_2O_3$ | 10 – 20. |

2. A dental filling composition according to claim 1, said glass ceramic containing more than 15% $La_2O_3$ to not more than about 20%.

3. A dental filling composition according to claim 1, said glass ceramic having the following composition in percent by weight:

| $SiO_2$ | 40 – 50 |
|---|---|
| $Al_2O_3$ | 16 – 20 |
| $Li_2O$ | 3.3 – 4.7 |
| $P_2O_5$ | 4 – 7 |
| MgO | 0 – 2 |
| ZnO | 0 – 5 |
| $ZrO_2$ | 3 – 6 |
| $Ta_2O_5$ | 2 – 6 |
| $La_2O_3$ | 13 – 18 |
| MgO + ZnO | 1 – 7. |

4. A dental filling composition according to claim 1, having a particle size of 5–60 microns.

5. A dental filling composition according to claim 1, having an X-ray mass absorption coefficient (0.2–0.3 A) of about 3 to 7.

6. A dental filling composition according to claim 4, having an X-ray mass absorption coefficient (0.2–0.3 A) of about 3 to 7.

7. A dental filling composition according to claim 1, having about 40–50 percent crystallinity by weight.

8. A dental filling composition according to claim 6, having about 40–50 percent crystallinity by weight.

9. A dental filling composition according to claim 1, having not more than about 17% by weight $La_2O_3$.

10. A dental filling composition according to claim 2 having not more than about 17% by weight $La_2O_3$.

11. A dental filling composition according to claim 1, containing more than 12% $La_2O_3$.

12. A dental filling composition according to claim 1, wherein the organic compound is at least one of acrylic acid, methacrylic acid, esters thereof or glycidyl adducts thereof.

13. A dental filling composition according to claim 2, wherein the organic compound is at least one of acrylic acid, methacrylic acid, esters thereof or glycidyl adducts thereof.

14. A dental filling composition according to claim 3, wherein the organic compound is at least one of acrylic acid, methacrylic acid, esters thereof or glycidyl adducts thereof.

15. A polymerized molded article of a composition defined by claim 12.

* * * * *